United States Patent [19]
Herleikson

[11] Patent Number: 5,682,902
[45] Date of Patent: Nov. 4, 1997

[54] ECG PACE PULSE DETECTION AND PROCESSING

[75] Inventor: Earl C. Herleikson, Yamhill, Oreg.

[73] Assignee: Hewlett-Packard Company, Palo Alto, Calif.

[21] Appl. No.: 543,738

[22] Filed: Oct. 16, 1995

[51] Int. Cl.$^6$ .................................................. A61B 5/0456
[52] U.S. Cl. ........................ 128/708; 128/697; 128/901
[58] Field of Search ........................ 128/697, 703, 128/704, 708, 901, 902; 607/27

[56] References Cited

U.S. PATENT DOCUMENTS

| | | |
|---|---|---|
| 3,780,737 | 12/1973 | King . |
| 3,923,041 | 12/1975 | Stasz et al. . |
| 3,986,496 | 10/1976 | Brastad . |
| 4,105,023 | 8/1978 | Marchese et al. . |
| 4,243,045 | 1/1981 | Maas ............................ 128/696 |
| 4,527,567 | 7/1985 | Fischler et al. . |
| 4,539,999 | 9/1985 | Mans ............................ 128/696 |
| 4,574,813 | 3/1986 | Regan .......................... 128/697 |
| 4,585,001 | 4/1986 | Belt . |
| 4,664,116 | 5/1987 | Shaya et al. . |
| 4,832,041 | 5/1989 | Wang et al. .................. 128/697 |
| 5,033,473 | 7/1991 | Wang et al. .................. 128/696 |

FOREIGN PATENT DOCUMENTS

| | | | |
|---|---|---|---|
| 0280529A2 | 2/1988 | European Pat. Off. .......... | A61B 5/04 |
| 0457524A1 | 5/1991 | European Pat. Off. ......... | A61B 5/043 |
| 1596821A | 1/1978 | United Kingdom ............. | A61B 5/04 |

Primary Examiner—Jeffrey R. Jastrzab
Attorney, Agent, or Firm—Scott K. Peterson

[57] ABSTRACT

A flexible ECG monitoring system including pace pulse detection. The monitoring system includes a potable monitor 102 that can be worn by a patient 120 or connected to a docking station 104. The portable monitor 102 includes an A/D converter 210, 208 and a digital signal processor 202. ECG signals are digitized and the digital signal processor derives a signal that is an estimate of the slope of the ECG signal. Pace pulses are detected by processing the slope signal, including use of a threshold that is dynamically updated based on the recent history of the slope signal. Detected pace pulses are removed prior to certain ECG filtering and reinserted following such filtering.

14 Claims, 7 Drawing Sheets

ECG PACE PULSE DETECTION AND PROCESSING

FIELD OF THE INVENTION

The present invention relates to the processing of electrocardiogram (ECG) signals, especially in cases where the EGG signal includes artifacts from a cardiac pacemaker.

BACKGROUND

Tools for measuring and processing ECG signals provide valuable information for healthcare professionals. The heart's pumping function is controlled by electro-chemical activity within the heart. This electro-chemical activity can be sensed as electrical signals at electrodes (usually placed on the body's surface, but the electrodes may also be invasive). These signals are know as electrocardiogram or ECG signals. Analysis of ECG signals can indicate many aspects of heart condition (for example, disturbances in electrical activation of the heart, or enlargement of heart chambers) that can adversely affect the heart's ability to pump blood through the body.

With some patients, such as those with serious rhythm disturbances, electrical devices are used to stimulate heart contraction. The electrical action of these artificial 'pacemakers' manifests itself in the ECG signal as an artifact known as a pace pulse. Pace pulses are typically of short duration (0.1 to 2.5 millisecond), have high frequency content, and have a low duty cycle (generally less than 2 pulses every 240 milliseconds, as used for dual chamber pacing at 250 bpm).

It is desirable to identify pace pulses in ECG signals. One reason for identifying pace pulses is so that they can be removed from the ECG signal. ECG signals are small in amplitude and often suffer from interference from many sources (for example, power lines, other electrical devices, electrical activity in muscles other than the heart); in attempt to separate out that part of the signal that is indicative of heart activity, EGG signals are subjected to filtering. When a pace pulse is subjected to the low pass filtering that is typically applied to an ECG signal (as is often useful in reducing muscle artifact), rather than eliminating the pace pulse, the pace pulse can be significantly widened. When a pace pulse is subjected to high pass filtering (as is often used in reducing baseline wander), a tail on the pace pulse can be created. These transformed pace pulses can reduce the reliability of subsequent ECG analysis, such as by being incorrectly recognized as a QRS complex (that portion of the ECG waveform associated with contraction of the heart's ventricles). Pace pulse detection can be used to help distinguish between QRS complexes and pace pulse tails, as described in U.S. Pat. No. 5,033,473 titled "Method for Discriminating Pace Pulse Tails". U.S. Pat. No. 4,838,278 titled "Paced QRS Complex Classifier" describes other ways that information from a pace pulse detector can be used in EGG processing. Many techniques have been used to detect pace pulses, such as the following. U.S. Pat. No. 4,574,813 titled "Pace Pulse Signal Conditioning Circuit" describes an approach using special-purpose analog circuitry to detect and replace pace pulses. U.S. Pat. No. 4,664,116 titled "Pace Pulse Identification Apparatus" describes an approach that compares a high-pass filtered ECG signal with a variable threshold. U.S. Pat. No. 4,832,041 titled "Pace Pulse Eliminator" describes an approach that uses a combination of a pace pulse detector based on special-purpose analog circuitry with a software-implemented pace pulse detection algorithm; the algorithm estimates ECG slope and compares it to a slope threshold that is based on detected QRS complexes.

SUMMARY OF THE INVENTION

According to the present invention, a patient's ECG signal is measured and converted to digital form. The digitization rate, higher than typically used for ECG analysis, is high enough to represent most pace pulses. From this digitized ECG signal, a signal is derived that is an estimate of the slope of the ECG signal. A slope threshold is computed and repeatedly updated based on the recent history (generally, shorter than the expected time between pace pulses that are to be detected) of the ECG slope signal; thus, the threshold rapidly adjusts to changes in the EGG noise environment. A pace pulse is identified when the magnitude of the slope signal exceeds the threshold at two points that are within about 3 milliseconds of each other and the slope at these two points is of opposite polarity.

After detection, a pace pulse is removed prior to certain ECG filtering and reinserted following such filtering. As an alternative to reinsertion, parameters measured from the pace pulse can be passed along with the EGG data. These techniques for dealing with pace pulses permit the ECG to be transmitted, stored, and processed using a relatively low amount of data or bandwidth, while still providing accurate pace pulse information; further, the pace pulse reinsertion alternative provides an particularly accurate pace pulse representation.

One challenge that pace pulse detectors have is to avoid triggering on a narrow R-wave (the pulse in the middle of the QRS complex). The present invention's combination of 2-slope detection and rapid threshold adaptation results in particularly high rejection of narrow R-waves. Although a narrow R-wave may have a very steep slope, the R-wave will generally be wide enough that, by the time its second edge would be detected, an initial portion of the R-wave will be have been included in the slope threshold determination; this is likely to increase the slope threshold such that the second edge will not exceed the threshold.

Many prior systems used specialized analog circuitry for pace pulse detection. In contrast, a system according to the present invention detects pace pulses without the need for analog components beyond those in the main ECG digitization signal path. In addition to reducing the amount of required circuitry (which may provide both cost savings and size reduction), this approach permits system upgrades, including to the pace pulse processing part of the system, to be accomplished by changing software in the system (for example, changes to analog circuitry are generally more difficult than reprogramming or replacing a ROM).

Further, pace pulse detection according to the present invention does not require R-wave detection information. Thus, the present approach to pace pulse detection is particularly useful in systems where R-wave detection occurs in a part of the system that is separated from where the pace pulse detection occurs (as may be the case in a telemetry system where pace pulse detection occurs in the telemetry unit and R-wave detection does not occur until the ECG signal reaches the central station).

BRIEF DESCRIPTION OF THE DRAWING

The invention is pointed out with particularity in the appended claims. The above and other advantages of the invention may be better understood by referring to the following detailed description in conjunction with the drawing, in which:

DETAILED DESCRIPTION OF AN ILLUSTRATIVE EMBODIMENT

The invention will be described in detail in the context of a flexible patient monitoring system that combines some of the attributes of an ECG telemetry system and some of the attributes of a bedside monitoring system.

Overall Patient Monitoring System

Figure 1:
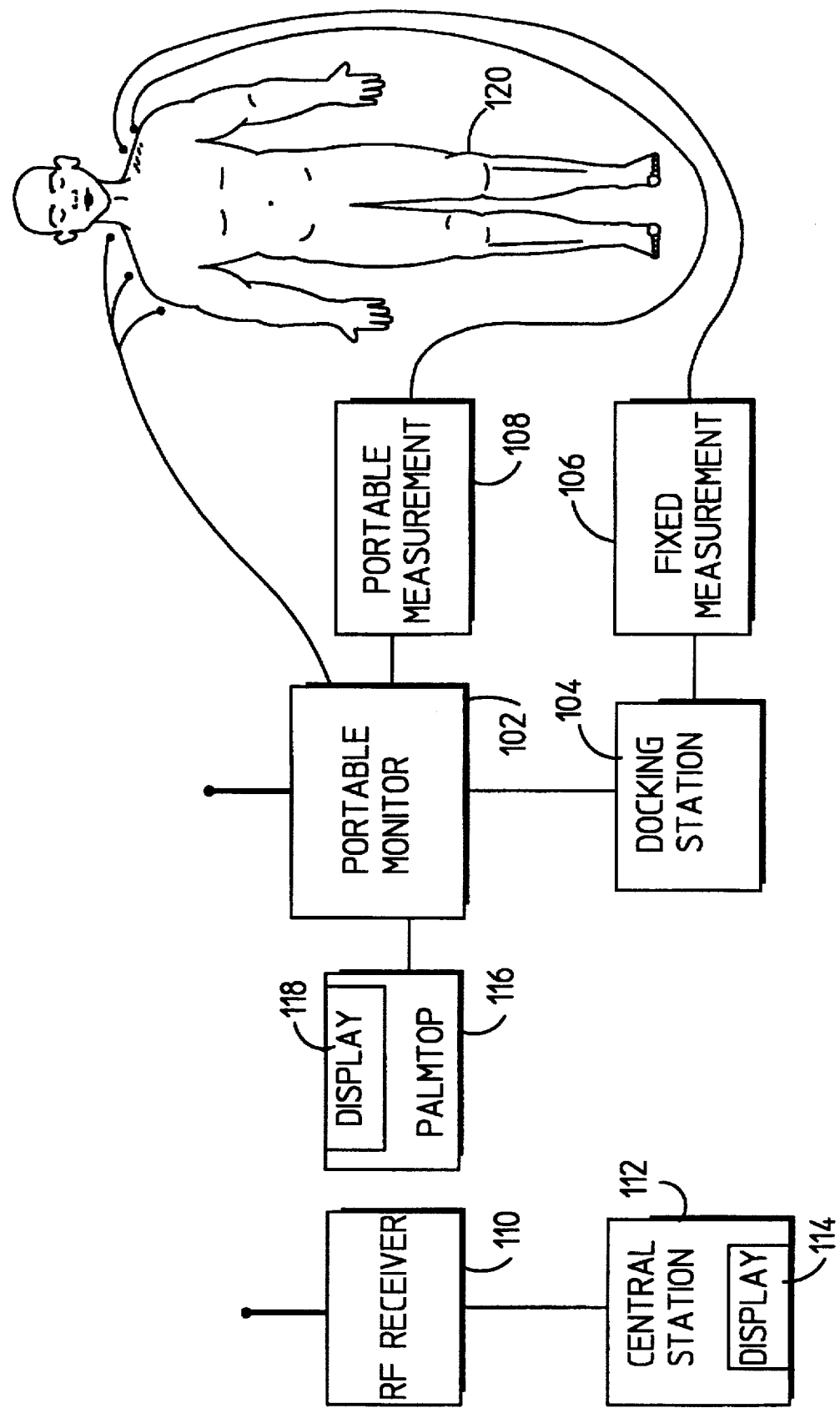
FIG. 1 is an overall block diagram of an ECG monitoring system.

The overall patient monitoring system is illustrated in FIG. 1, and includes a portable monitor 102, a central monitoring station 112, and a docking station 104. These components can be connected to instruments for measuring parameters beyond those measured by the portable monitor 102 and can be connected to other patient-related equipment (for example, ventilators).

The portable monitor 102 is battery-powered and is sufficiently compact that it can be carded by a patient 120. Electrical leads connect the portable monitor 102 to ECG electrodes on the patient 120. Portable measurement devices 108 having circuitry for measuring additional parameters of a patient can be connected to the portable monitor 102; alternatively, circuitry for additional measurements can be integrated directly into the portable monitor 102.

The central monitoring station 112 includes a display 114 for healthcare professionals to view data (for example, ECG signals) from a number of patients. The central monitoring station 112 is connected to a wireless receiver 110 (typically RF, although other wireless technologies could be used) that receives patient data from one or more portable monitors 102.

The docking station 104 sits at a patient's bedside. It is connected to power and to other equipment 106 located at the patient's bedside (for example, instruments for making additional measurements from the patient 120 or equipment such as ventilators or infusion pumps). When the patient 120 is in bed, the portable monitor 102 can be connected to the docking station 104; when connected, the docking station 104 can provide power to the portable monitor 102 and can exchange data with it.

Data flows from the electrodes (and any other sensors connected to the portable monitor 102) to the portable monitor 102, and then by wireless connection from the portable monitor 102 to the central station. Data from bedside equipment flows from the patient 120 to that equipment, to the docking station 104, to the portable monitor 102, and then to the central station. In addition, information could flow in the reverse direction (for example, to permit someone at the central station to make adjustments in any of the equipment).

A small device 116 with a display 118 and computing capability (such as a palmtop computer) can be connected to the portable monitor 102 to provide a display of ECG signals and other data and to provide an enhanced user interface for interaction with the portable monitor 102 (such as to configure it and make adjustments). Similarly, such a device 116 could be connected to the docking station 104.

In addition, the monitoring system can include a conventional bedside monitor. The bedside monitor could be connected to the docking station 104 (to send data to the portable monitor 102 for RF transmission to the central station) and/or could be connected via conventional wiring to send data to the central station, including data from the portable monitor 102.

The various connections among the system components can be via direct electrical connection or can be via wireless communication links (for example, using infra-red or RF).

Portable Monitor

Figure 2:
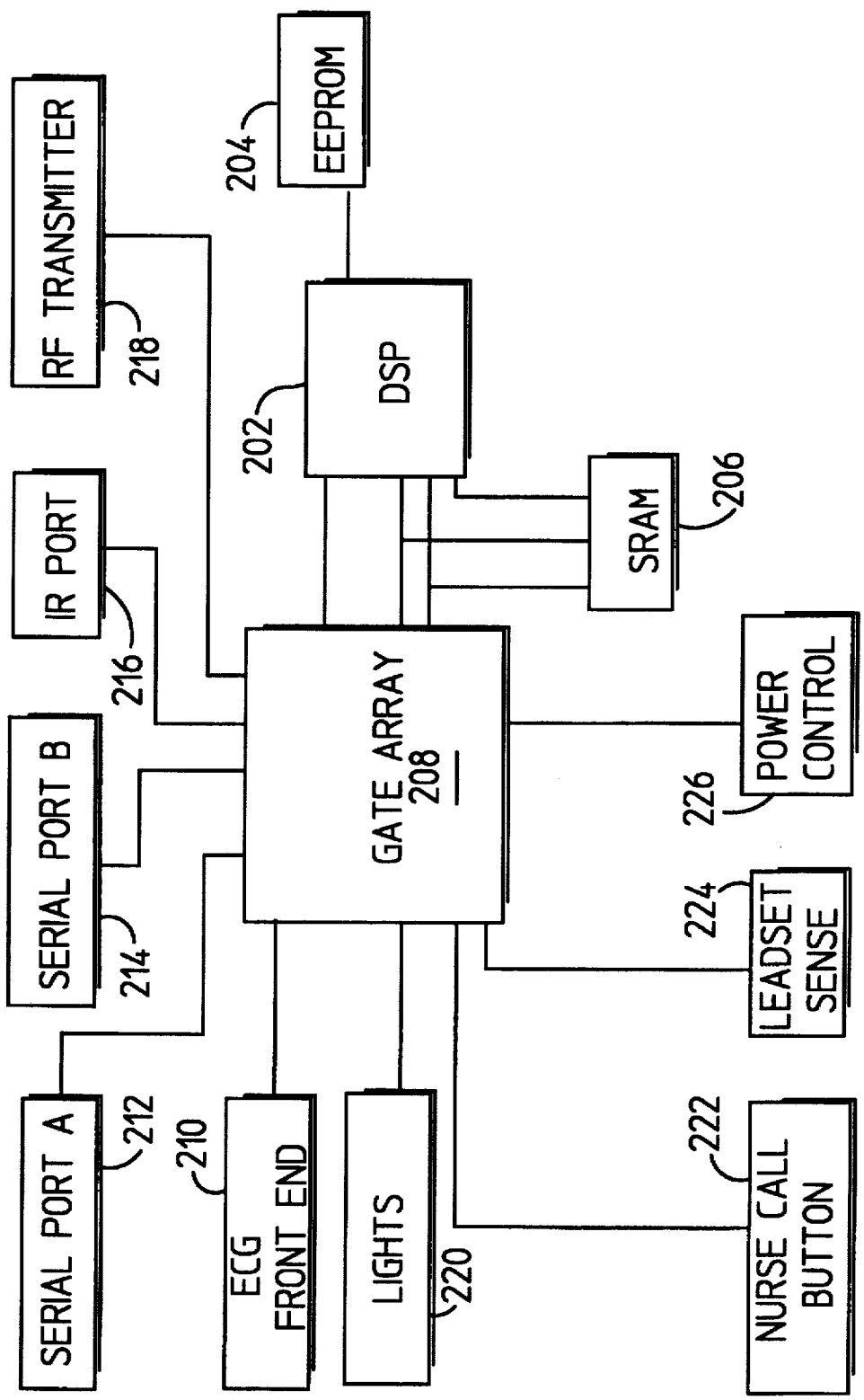
FIG. 2 is a block diagram of a portable monitor component of an ECG monitoring system in which the present invention is implemented.

The organization of the circuitry of the portable monitor 102 is illustrated in FIG. 2, and includes several serial ports 212, 214, 216, an RF transmitter 218, power control circuitry 226, five indicator lights 220, a nurse-call button 222, a leadset sensor 224, and ECG front-end circuitry 210. A digital signal processor (DSP) chip 202 is connected to these via a gate array chip 208, which implements a variety of functions.

The DSP 202 (for example, a Motorola DSP56007) can boot directly from a serial EEPROM, a feature that allows for easy upgrades through a serial port. In addition to memory on the DSP chip itself, there is an 8K×8 bit serial EEPROM 204 and a 32K×8 bit SRAM 206. The EEPROM 204 stores the unit's unique identifier, patient information, and DSP patch code (permitting the DSP's programmed operation to be upgraded by reprogramming the EEPROM).

The serial ports 212, 214, 216 provide for both direct electrical connection 212, 214 as well as wireless connection (for example, via infra-red light) 216 to other devices. The parameters measured by the portable monitor 102 can be extended by connecting a serial port 212 to portable measurement front-ends such as for measuring SpO2. The portable monitor 102 can also be connected to relatively fixed equipment such as bedside monitors or other standalone instruments 106. In addition, it can be connected to a device such as a palmtop computer 116 that can provide an enhanced user interface for interaction with the portable monitor 102 and can display signals measured by the portable monitor 102; the IR port 216 is particularly suited to provide an easy way to make a temporary connection to the portable monitor 102. Finally, a serial port 214 can provide a connection to the docking station 104, which then provides connection to other equipment. These ports provide means for sending signals from the portable monitor 102 to other equipment, and the ports provide means for receiving signals from other equipment, in which case the RF transmitter 218 in the portable monitor 102 can be used to send (to the receiver 110 and then to the central station 112) measured parameters in addition to those measured by the portable monitor itself.

The five indicator lights 220 (LEDs) connected to the gate array 208 such that they can be turned on and off by the DSP 202. These indicator lights can be used to give leads-off indications. In addition, they can be used to indicate R-wave detection and pace pulse detection.

The nurse-call button 222 can be read by the DSP 202 via the gate array 208.

The leadset connector in the portable monitor 102 includes a number of switches 224. Different types of leadsets close different combinations of switches in the connector. These switches 224 are connected to the gate array 208, which permits the DSP 202 to automatically configure its ECG processing according to the type of leadset used (for example, for 3, 4, or 5 electrodes).

To facilitate power conservation, switches 226 for controlling power to various parts of the portable monitor 102 are connected to the gate array 208. For example, when not used, the RF circuitry 218 can be powered off.

The gate array 208, the ECG front-end 210, and the DSP 202 are described in more detail below.

Gate Array

Figure 3:
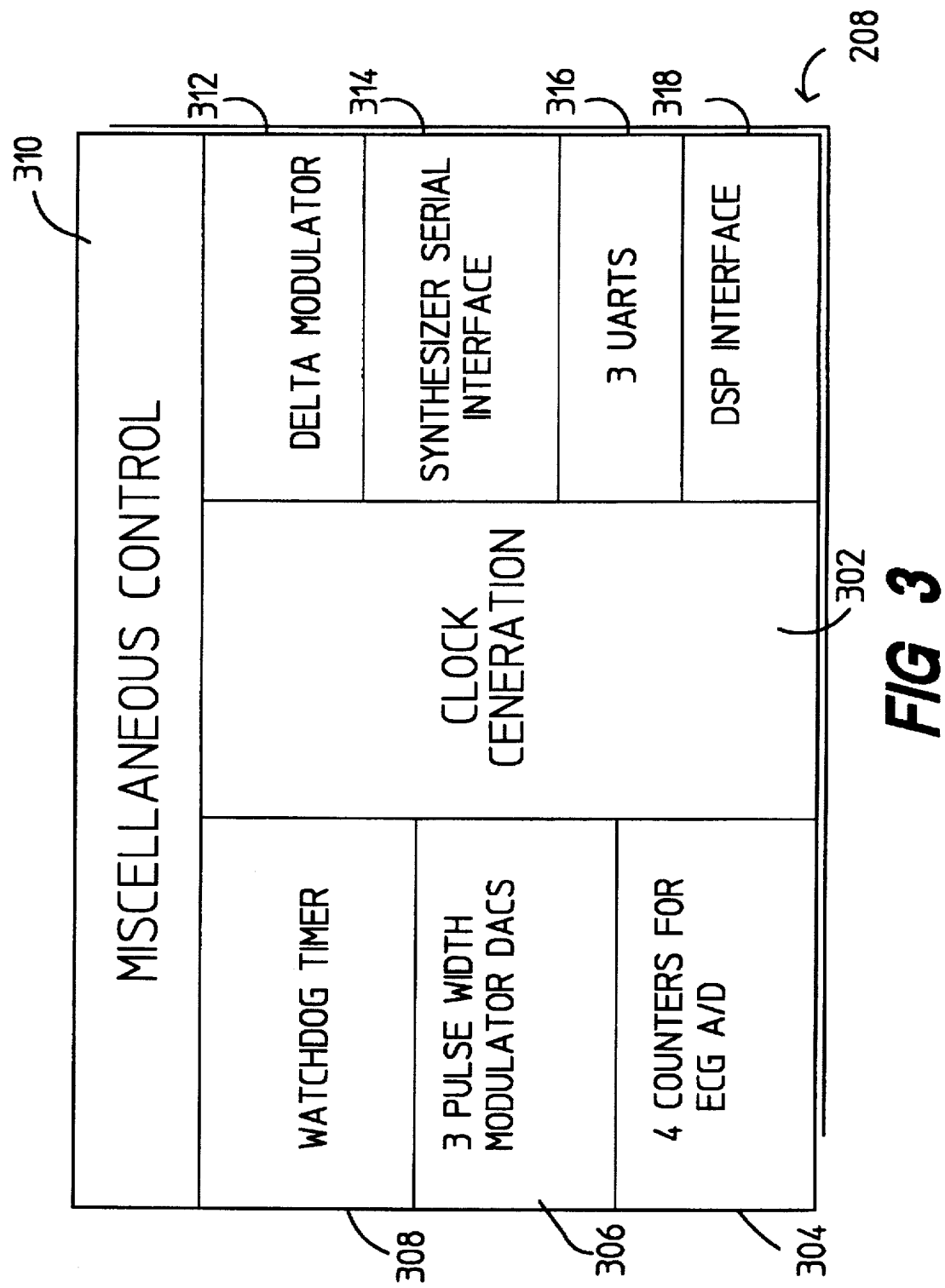
FIG. 3 is a block diagram of the functional organization of a gate array in the portable monitor.

As illustrated in FIG. 3, the gate array 208 includes circuitry to perform a variety of functions, including generation of clock signals 302, a watchdog timer 308, three pulse-width modulator DACs 306, four counters for the ECG A/D converters 304, a delta modulator 312, an interface for control of a synthesizer 314, three UARTs 316, and an interface 318 to the DSP 202. In addition, the gate array 208 includes miscellaneous control circuitry 310.

The synthesizer interface 314 provides support for control of the RF transmitter 218 that uses, for example, a Motorola MC 145192 synthesizer chip. The delta modulator 312 is used for formatting a serial data stream appropriate for RF transmission.

The watchdog timer 308 is included so that the gate array 208 will reset the DSP 202 if the DSP does not communicate properly with the gate array for some period of time.

There is circuitry in the gate array 208 that provides the following signals for each of the four ECG measurement channels: switch control signals (switch control A) to enable connection of the right leg drive signal to that channel's electrode (for calibration), a pulse width modulated low frequency feedback signal, a high frequency feedback signal. There are four additional signals for the right leg drive: one to connect a calibration signal to the right leg drive circuit (calibration switch control) and three to select the measurement channels to be used for input summation to create the right leg drive signal (switch control B).

The gate array 208 counts the number of 6.4 MHz clock cycles when the A/D comparator output is high for each 8 KHz clock cycle. The comparator output (from the ECG front end, described below) is latched on the rising edge of 6.4 MHz clock, and is counted on the other edge. This latched signal is output as a feedback signal for both the high frequency feedback and low frequency feedback. The high frequency feedback signal performs the function of an 11-bit A/D at a 4 KHz conversion rate (conversion values range from 0 to 1600). The low frequency feedback has a bandwidth of 222 Hz and a open loop gain of 33.6.

The pulse-width modulator DACs 306 are used to calibrate the ECG measurement. One DAC is used for the RA measurement channel, one is used for the LA measurement channel, and the third DAC is used for both the LL and V measurement channels. The number of these DACs is largely determined by available space on the gate array. Because the calibration can be done one channel at a time, a single DAC could be used.

To calibrate the ECG measurement, the gate array 208 performs two separate functions. For both, all four right leg drive switches are closed. First the low frequency feedback signal is disconnected from the latched A/D output and connected to a pulse-width modulated signal from one of the DACs 306. This pulse-width modulated signal applies a known step function to the 6.6 Hz low pass filter to calibrate both the open loop gain and corner frequency. The second calibration function is to sum a calibration signal at the right leg drive integrator. This causes a step voltage to occur on all four channels. With this step change, the gain difference of all channels can be corrected.

ECG Front-end

Figure 4:
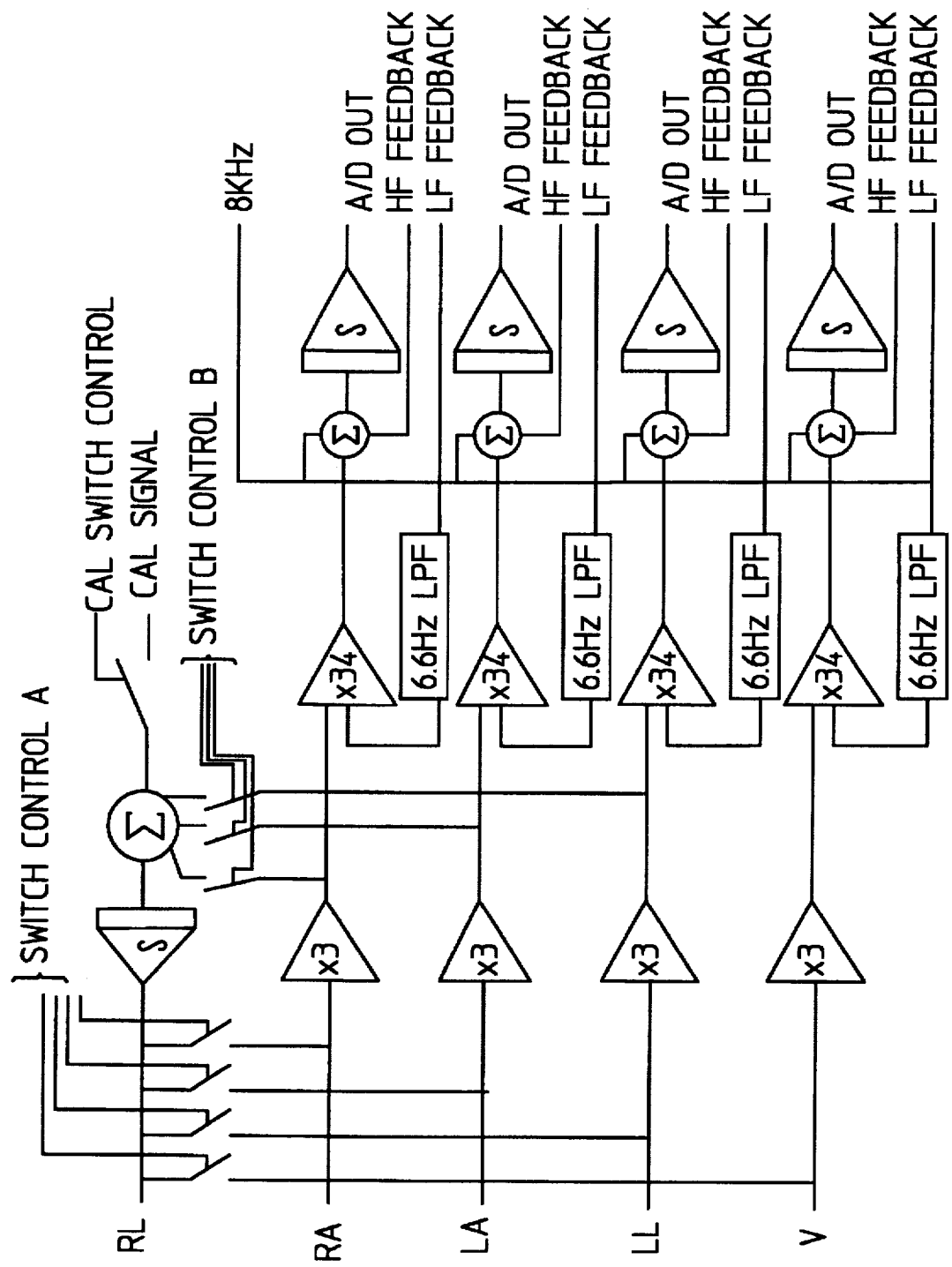
FIG. 4 is a block diagram of an ECG front-end in the portable monitor.

As illustrated in FIG. 4, the portable monitor 102 includes circuitry to generate a right-leg drive signal for connection to one of the ECG electrodes (RL) and input circuitry for connection to four other ECG electrodes (RA, LA, LL, and V).

The right-leg drive circuit sums one to three of the ECG inputs to generate one output that is connected to an ECG electrode; in addition, switching circuitry is provided to permit the right-leg drive signal to be connected to any of the four input electrodes. The right-leg drive signal is used to improve the common mode rejection performance of the ECG front-end. The ground reference of the right-leg drive amplifier can be switched to a calibration voltage and connected to the inputs to all four of the ECG measurement channels. By measuring the calibration signal applied to all channels, the gain difference of all four A/D channels can be corrected in software. This calibration is important because, clinically, the ECG measurement is analyzed by 'leads', each of which consists of the difference between the signal at one electrode and the signal at one or more other electrodes; calibration enhances the ability of this difference operation to removed common mode signals, which can be large compared to the size of the desired ECG signal.

The input circuitry for each of the four input electrodes operates with the gate array 208 to convert each of the four analog inputs to digital signals with a data rate of 4,000 samples per second and a least-significant bit (LSB) resolution of 16 microvolts; after decimation to a 500 Hz data rate, the LSB resolution becomes 2 microvolts due to the fact that adjacent samples of an integrating A/D are correlated. Referring to FIG. 4, each of the 4 A/D converters sends a A/D out signal to the gate array 208; the gate array 208 generates signals that are used by the input circuitry: a calibration signal, a fixed 8 KHz 50% duty cycle square wave, a low frequency feedback signal for each of the four input channels, and a high frequency feedback signal for each of the four input channels.

The input circuitry for each of the four input electrodes includes input protection, a 3 KHz low pass filter, a leads-off current source of 25 nA through a 100M resistor. This is followed by a first stage which is an input buffer amplifier with a gain of 3 and an output range of 0.77 to 3.23 volts. The input buffer amplifier is followed by a summing junction to sum the low frequency feedback signal containing 1.5 mVpp of 8 KHz ripple, which is then amplified by a factor of 16. Finally the signal is converted to a 11-bit digital word with a pulse-width modulation sigma delta A/D having a null response to the 8 KHz ripple of the feedback signal. The latched comparator output of the A/D is the low frequency feedback signal which closes a loop around the gain stage and the A/D. This means that the final digitized signal will have a DC gain set by the low frequency feedback signal accuracy, a zero at 6.6 Hz and a pole at 222 Hz (6.6 Hz times the open loop gain of 33.6). Only two values need be measured in order for the DSP to be able to compensate this response: the 6.6 Hz pole and open loop gain are both measured by opening the loop and providing a single step input and calculating the step response at the output. The final result is a A/D with a dynamic range of +−0.41V from DC to 6.6 Hz decreasing to 12.8 mV at 222 Hz.

The low frequency feedback summing amplifier sums the low frequency feedback signal with the signal from the input buffer amplifier and provides a gain of about 34 (there is a factor of about 2 gain at the summing junction, while the opamp itself provides a gain of about 16, with the resulting total gain being about 34). The gate array 208 generates a low frequency feedback signal by pulse width modulating an 8 KHz square wave switching between +1.235 and −1.235 volts. The resolution of the pulse width is set by a 6.4 MHz clock, resulting in a step size of 3 mV (1 mV when referred to the input to the input buffer amplifier). The low frequency feedback signal is derived directly from the 1-bit comparator output of the A/D converter. The low frequency feedback signal passes through a low pass filter with a single pole at 6.6 Hz before arriving at the input of the summation amplifier. The open loop gain of this feedback signal is about 34. The closed loop bandwidth is thus 222 Hz. Because this feedback signal is digitally connected through the gate array 208, the loop can be opened and a known set of pulse width modulated signals can be applied to measure the open loop gain and the time constant of the 6.6 Hz pole. The gain accuracy of the A/D converter is set by the accuracy of the low frequency feedback signal, including voltage and timing.

The final stage of the input circuitry could be called a pulse width modulated sigma delta A/D converter. There are three signals summed together into the inverting input of an integrating opamp whose output drives a comparator. The first signal is the signal to be digitized (the original input to which the low frequency feedback signal has been added). The second signal is the high frequency feedback signal derived from the comparator output. The third signal is a fixed 8 KHz 50% duty cycle square wave. Ignoring the third signal, this circuit would be a simple sigma delta A/D converter. The comparator behaves as a 1-bit A/D with a conversion rate of 6.4 MHz. This 1-bit A/D value is used as a feedback signal (the high frequency feedback) to the input of the integrating opamp such that over time, the average must equal the input signal. Assuming an ideal comparator, the comparator output could toggle at a rate as high as the 6.4 MHz clock rate. By adding a 8 KHz fixed square wave to the summing junction with twice the amplitude of the feedback signal, the comparator will change state only twice during one period of the 8 KHz clock cycle. This significantly reduces the speed and accuracy requirements of the comparator and also reduces the response time of the A/D converter. The A/D value is simply determined by counting the number of 6.4 MHz clock cycles when the comparator output is a one, which is done by a counter in the gate array 208. Because the summation of the high frequency feedback signal is half that for the input signal (and half that for the fixed 8 KHz signal), this final stage has a gain of two. With a range of +−1.235V for the feedback signal, the input range is +−12.8 mV referred-to-input.

The time constant of the A/D converter is half the period of the 8 KHz clock or 62.5 microseconds. This translates to a single pole low pass filter of 2.5 KHz. Because the average of the data over the 8 KHz period determines the A/D value, there is a null in the frequency response of the A/D at 8 KHz and every harmonic of 8 KHz. The mathematical description is sin(pi*8 KHz/f)/(pi*8 KHz/f). This makes for excellent anti-alias rejection capability. For example, with a 125 Hz low pass filter for the ECG data, a signal 125 Hz away from 8 KHz will be rejected by 125/8000=−36 dB. Then add the attenuation due to the 3 KHz low pass filter at the input and the 2.5 KHz low pass filter created by the 8 KHz A/D converter and the anti-alias rejection becomes 55 dB.

Signal Processing by the DSP

Figure 5:
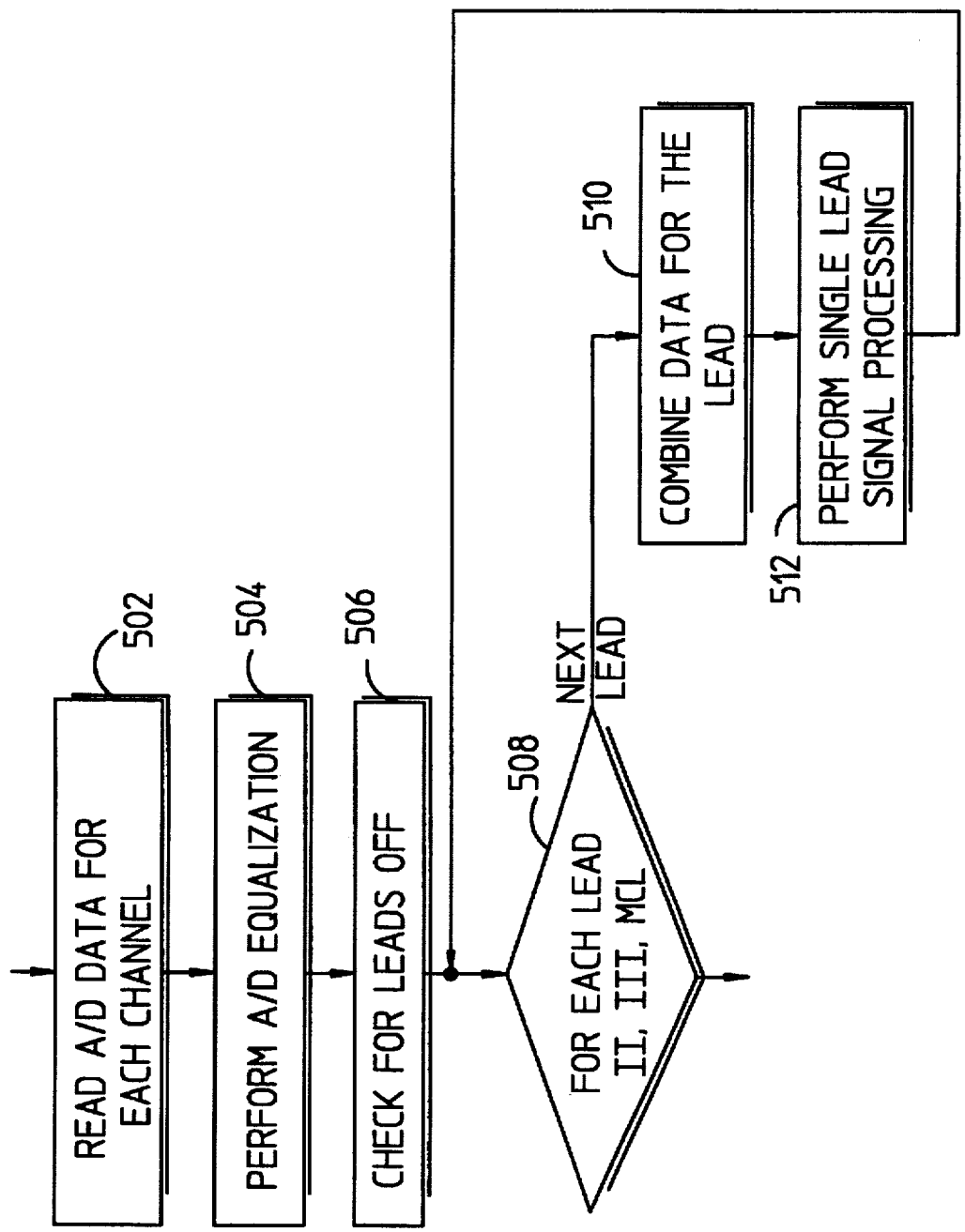
FIG. 5 is a flow chart showing overall ECG signal processing.

Once the ECG signals are converted to digital form, subsequent processing by the portable monitor 102 is done on the digital form of the ECG signals. Referring to FIG. 5, the DSP 202 reads (from the gate array 208) the data from the four A/D converters 502, with each sample of each of these four signals being stored in one 16-bit word. These four signals are each is multiplied by its calibration constant, corrected for the measured pole zero response of the low frequency feedback 504. In addition, once every 32 milliseconds these signals are evaluated to determine if any are in a leads-off state 506. Signals representing each of the clinical 'leads' II, III and MCL are generated by combining 508, 510 the signals from the four measurement electrodes. Each of these three lead signals is then processed 508, 512, as illustrated in more detail in FIG. 6.

Figure 6:
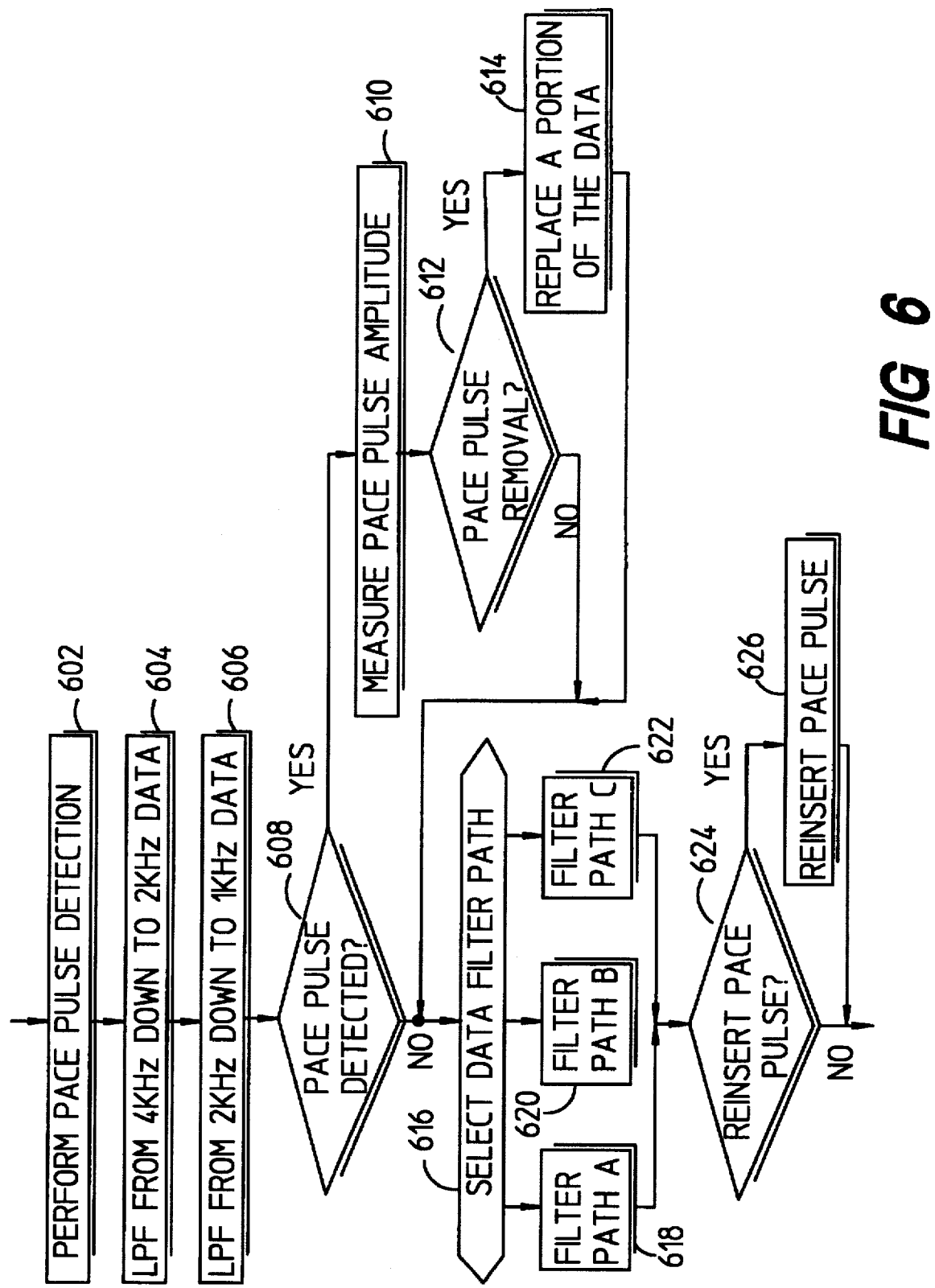
FIG. 6 is a flow chart showing signal processing that is performed for each ECG lead.

Referring to FIG. 6, each of the 'lead' signals is used for pace pulse detection 602 (described in more detail below in connection with FIG. 7) prior to the further low pass filtering 604, 606 that is used to condition them for transmission, display, and/or other processing.

In two stages 604, 606 (each with a finite impulse response filter and decimation by two), the streams of 4000 samples per second are reduced to streams of 1000 samples per second.

When a pace pulse is detected 608, then pace pulse related processing of ECG signal occurs 610, 612, 614, 624, 626 as described below.

In the illustrative embodiment, the portable monitor 102 can send data through the IR port 216 and it can send data through the RF transmitter 218 using either of two alternative RF protocols. Thus, one of several signal processing sequences 618, 620, 622 is selected 616 for further processing of the 1000-sample-per-second signals. This processing 618, 620, 622 includes further low pass filtering and decimation (for example, to 40 Hz at 250 samples per second, 125 Hz at 500 samples per second, or 100 Hz at 400 samples per second), an optional line frequency notch filter (for example, at 50 Hz or 60 Hz), and processing according to the communication protocol being used to send the data to another part of the ECG monitoring system or to another device.

Pace Pulses

Pace pulses have short duration (0.1 to 2.5 milliseconds) and high frequency content (2 KHz band pass filtering can be used for hardware-based pace pulse detection) and have low duty cycle (for example, there are only two pulses every 240 milliseconds with dual chamber pacing at 250 beats per minute). The best place to deal with this data is as close to the ECG front-end as possible, before any reductions in sample rate or any low pass or high pass filtering. Low pass filtering can widen the pace pulse and high pass filtering can create a tail following the pace pulse. This may make the pace pulse look more like an R-wave; such changes can interfere with automated signal analysis to detect arrhythmias.

The illustrative embodiment detects pace pulses using high data representation of the ECG signal (4 KHz sample rate). It then offers two alternatives for dealing with pace pulses when the data is reduced to a lower sample rate for subsequent processing: (1) a detected pace pulse can be removed from the ECG signal prior to filtering, and then reinserted after such filtering; (2) a detected pace pulse can be measured, removed from the ECG signal, and then the measured pace pulse parameters can be used in subsequent processing. These techniques for dealing with pace pulses provide for accurate representations of pace pulses, while permitting the ECG to be transmitted, stored, and processed using a relatively low amount of data or bandwidth.

Pace Pulse Detection

This illustrative embodiment is designed with the goal of detecting pace pulses of amplitudes from 0.5 mV to 700 mV and widths of 0.5 millisecond to 2.5 milliseconds. It is very desirable to detect pace pulses having widths from 0.1 millisecond to 0.5 millisecond, but in this illustrative embodiment the amplitudes at which the narrow pulses will be detected may degrade to 2 mV at widths of 0.1 millisecond.

Another design goal of the illustrative embodiment is rejection of false detection of any signal that is not a pace pulse. Possible sources for false detections are white noise, muscle artifact, very narrow R-waves, pulses at high rates such a 50/60 Hz line frequencies, or any periodic waveform of rate greater than 25 Hz.

In simplest terms, this pace pulse detector looks for positive and negative edges that occur within a certain time window and have an amplitude greater than 3 times peak magnitude of the last 64 milliseconds history of edges. The time window is set to be longer than the expected width of pace pulses to be detected; however, if the window is set arbitrarily large, the detector will trigger on R-waves or other pulses. In the illustrative embodiment, the positive and negative edges must occur within a time window of 3 milliseconds.

Figure 7:
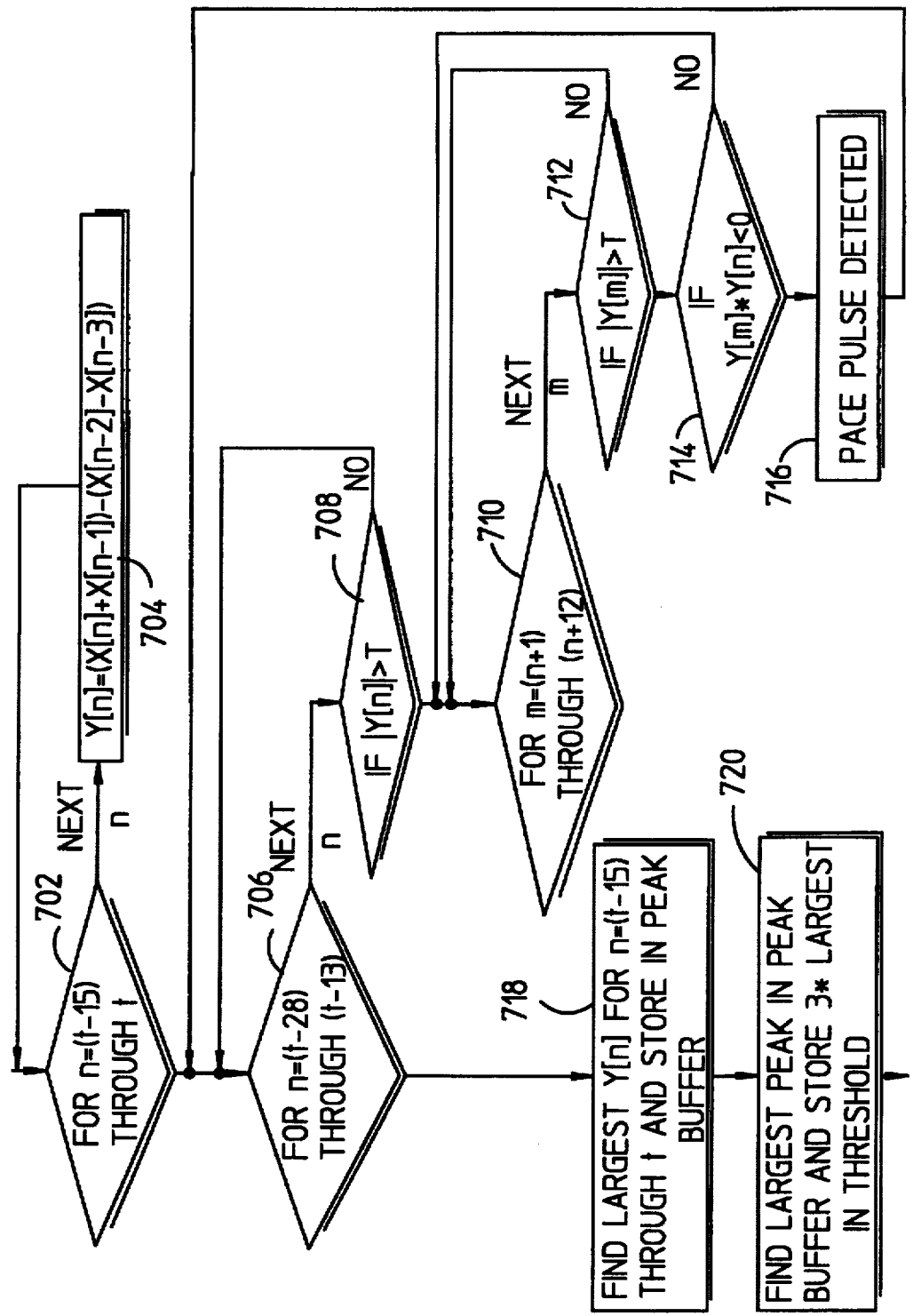
FIG. 7 is a flow chart detailing the steps of pace pulse detection.

FIG. 7 illustrates that part of the DSP's 202 signal processing that is focused on pace pulse detection. This processing is performed on each 4000-sample-per-second 'lead' (for example, II, III, and MCL), each of which is referred to as x[t] in the following description. For each lead, the processing illustrated in FIG. 7 is repeated every 16 samples; thus, each time that the processing in FIG. 7 is performed, 't' will be 16 samples (4 milliseconds) greater than the previous time.

The DSP 202 generates a signal that is an estimate of the slope of x[t]; this slope signal will be referred to as y[t]. The particular slope estimate used in the illustrative embodiment is generated by calculating y[n]=(x[n]+x[n−1])−(x[n−2]+x[n−3]) (block 704) for each of the 16 samples being processed 702.

The DSP 202 stores the most recent 32 values of y[t] (y[t] to y[t−31]) in a buffer. By maintaining a buffer of the most recent 32 values of y[t] (y[t] to y[t−31]), the updating of y[t] and the other steps of pace pulse detection can occur in blocks of 16 samples once every 4 milliseconds, rather than doing the processing once every 0.25 millisecond for a single sample.

The DSP 202 also maintains a 64 millisecond history of the slope magnitude peak (block 718). For storage efficiency, this slope peak history is maintained as a circular buffer of 16 slope magnitude peak values, each of these being the slope magnitude peak for a 4 millisecond interval. Thus, this slope magnitude peak buffer provides a history of 64 milliseconds, but a history that is updated only every 4 milliseconds. (This is a different buffer from that which stores the most recent 4 milliseconds of the slope signal itself.)

The DSP 202 uses the slope magnitude peak buffer to determine a slope threshold by identifying the largest value of those 16 peaks (of each of the 4 millisecond blocks) and then computing and storing 3 times that value (block 720). This remains the current threshold for processing 4 milliseconds of ECG signal. After processing of 4 milliseconds of ECG data, the slope magnitude peak for that 4 millisecond block is determined 718 and is stored in the slope magnitude peak buffer, and the threshold for the next 4 millisecond block of ECG data is then computed and stored 720. (When this ECG processing is started, there will be some initial values in the buffers that do not correspond to actual signals; however, once the processing is ongoing, the history data and the threshold will have been set based on processing the previous blocks of samples.)

The slope signal, y[t], is processed to search for pace pulses as follows. For each y[n] for n=(t−28) through n=(t−13) (block 706), if the magnitude (in other words, absolute value) of y[n] is greater than the current slope threshold (block 708), then y[n] is a candidate pace pulse edge. When a candidate pace pulse edge is located, the slope signal is searched for a second edge. The slope signal y[m] for m=(n+1) through m=(n+12) (block 710) is searched for the second edge (blocks 712 and 714). The second edge must have a slope greater than the current slope threshold (block 712), and must have a polarity that is the opposite of the polarity of the candidate edge (block 714). If a suitable second edge is located, then a pace pulse is detected (block 716).

Following is a pseudo-code summary of processing of the ECG signal to detect pace pulses that is done in blocks of 16 samples (t=current time; t increases by 16 each time this processing is performed for each lead):

```
For n=(t−15) through t
    y[n] = (x[n]+x[n−1]) − (x[n−2]+x[n−3])
    EndFor n
For n=(t−28) through (t−13)
    If |y[n]| > Threshold
        For m=(n+1) through (n+12)
            If |y[m]| > T
                If y[m]*Y[n]<0
                    Pace Pulse Detected
                    Stop looping over m
                EndIf
            EndIf
        EndFor m
    EndIf
EndFor n
For n=(t−15) through t
    Find largest y[n]
EndFor n
Store largest in PeakBuffer[current]
For n=0 through 15
    Find largest PeakBuffer[n]
EndFor n
Store 3*largest in Threshold
```

This pace pulse detection processing could be done on a sample-by-sample basis, or could be broken into blocks of processing other than 16 samples.

Pace Pulse Processing

When a pace pulse is detected 608, the pace pulse amplitude is measured 610 by taking the difference between the peak value of the pace pulse and the average of 2 milliseconds of signal data just prior to the pace pulse. When there is a repolarization pulse it may be desirable to calculate amplitudes for both the main and repolarization pulses. Other parameters of the pace pulse, such as its area, could also be measured. Such parameters together with a time marker can be passed along with the ECG data to be used in subsequent ECG processing, analysis and/or display. In addition, pace pulse detection can be indicated by momentarily lighting an indicator light 220.

If pace pulses are to be removed 612 from the ECG signal, then that removal is done 614 on the 4 KHz data. Removal is accomplished by replacing (starting just prior to the pace pulse) 12 milliseconds of signal. This interval is replaced with a flat signal level that is the average of 2 milliseconds of signal just prior to the pace pulse.

Pace pulses from certain types of pacemakers have a long repolarization tail. Rather than always removing a long enough period of time to remove such long pace pulses, the illustrative embodiment starts with a fixed 12 millisecond removal period, and detects certain conditions when that period should be extended, as follows. When a pace pulse is detected, the current threshold is stored in a location known as the 'delayed threshold'. If, during the pace pulse removal period, a slope is detected that exceeds the delayed threshold, then the removal period is extended so that it continues 12 milliseconds after this detected slope. Also, if such a slope is detected, at that time the delayed threshold is updated—in other words the then current threshold is again stored in the delayed threshold. This method results in certain pace pulse repolarization waves being detected; in that case the removal period is extended so that the repolarization wave is removed. A 'delayed threshold' is used because the threshold that would be current during the removal period would be based on data that included the main pace pulse itself and, thus, would be set too high (three times the maximum slope of the main pace pulse) to detect the repolarization wave. Updating the delayed threshold when something does exceed the delayed threshold prevents the following undesirable situation from occurring: if the detector initially triggers in a period of high frequency noise, the removal period could continue to be extended until the noise ends.

Once the ECG signal with pace pulses removed has been filtered 618, 620, or 622, it may be desired that the pace pulse be reinserted into the filtered data, 624. When a pace pulse is removed, a representation of the removed data is saved as follows: a signal is created for the time period of the removed data that is the difference between the 1 KHz signal (filtered from the 4 KHz signal without pace pulses) and the 4 KHz signal that contains the pace pulses; this 4 KHz data that represents the removed pace pulse is then reduced to the lower data rate of filter paths 618, 620, or 622 by adding together the 4 KHz samples that correspond to a sample at the lower data rate (peak picking, rather than averaging, could be used instead). A pace pulse is reinserted by adding this data to the ECG signal that results from filter paths 618, 620, or 622. Alternatively, a standard pace pulse could be reinserted, or a pace pulse reconstructed based on measurement of the actual pace pulse could be reinserted.

The foregoing has described a specific embodiment of the invention. Additional variations will be apparent to those skilled in the art. For example, although the invention has been described in the context of a particular patient monitoring system, it can also be used in other types of patient monitoring systems (including stand-alone bedside monitors not connected to any central station). Further, the invention could be employed in other systems that process ECG signals, such as a diagnostic cardiograph or a Holter monitor system. Other techniques can also be used for pace pulse removal, for example: the region of the pace pulse can be replaced by a linear interpolation between the end points of the region; an estimate can be made of the shape of the pace pulse and this estimate pulse can be subtracted from the EGG signal. Thus, the invention is not limited to the specific details and illustrative example shown and described in this specification. Rather, it is the object of the appended claims to cover all such variations and modifications as come within the true spirit and scope of the invention.

I claim:

1. Apparatus for detecting pace pulses in an ECG signal comprising:
   (A) means for processing the EGG signal to create a slope signal that is an estimate of the slope of the EGG signal;
   (B) means for repeatedly determining and updating a slope threshold, where the slope threshold is determined based on analysis of the slope signal over a time interval that is less than the time between pace pulses to be detected;
   (C) means for determining when the magnitude of the slope signal exceeds the threshold;
   (D) means for detecting when a positive slope that has been identified as exceeding the threshold is within a particular a time of a negative slope that has been identified as exceeding the threshold, where the particular time is based on expected widths of pace pulses to be detected.

2. The apparatus of claim 1 wherein the threshold is about three times the peak value of the slope over the interval analyzed.

3. The apparatus of claim 1 wherein the particular time is about three milliseconds.

4. The apparatus of claim 1 further comprising means for creating a modified ECG signal in which a portion of the signal having a detected pace pulse is substantially modified.

5. The patient monitoring system of claim 4 wherein the means for creating a modified ECG signal:
   (1) stores an initial threshold;
   (2) replaces ECG data for a predetermined replacement period;
   (3) in the replacement period, searches for a slope that exceeds the threshold, and if such slope is detected, extends the replacement period and replaces the initial threshold with a new value.

6. A method for analyzing an ECG signal from a patient to identify artifacts in the ECG signal resulting from artificial pacing of the patient's heart, comprising the steps of:
   (A) processing the EGG signal to create a slope signal that is an estimate of the slope of the ECG signal;
   (B) determining when the magnitude of the slope signal exceeds a threshold;
   (C) detecting when a positive slope that has been identified as exceeding the threshold is within a particular a time of a negative slope that has been identified as exceeding the threshold, where the particular time is based on expected widths of pace pulses to be detected;
   (D) updating the threshold, where the threshold is determined based on analysis of the slope signal over a time interval that is less than the time between pace pulses to be detected.

7. A computer-readable memory configured so that it can be used to direct a computer to analyze an ECG signal according to the following steps:
   (A) processing the ECG signal to create a slope signal that is an estimate of the slope of the ECG signal;
   (B) determining when the magnitude of the slope signal exceeds a threshold;

(C) detecting when a positive slope that has been identified as exceeding the threshold is within a particular a time of a negative slope that has been identified as exceeding the threshold, where the particular time is based on expected widths of pace pulses to be detected;

(D) updating the threshold, where the threshold is determined based on analysis of the slope signal over a time interval that is less than the time between pace pulses to be detected.

8. A patient monitoring system comprising:

(A) ECG front-end for connecting to electrodes to measure an analog ECG signal from a patient and convert that analog ECG signal to a digital ECG signal;

(B) a pace pulse detector comprising means for processing the digital ECG signal to create a slope signal that is an estimate of the slope of the ECG signal, means for repeatedly determining and updating a slope threshold, where the slope threshold is determined based on analysis of the slope signal over a time interval that is less than the time between pace pulses to be detected, means for determining when the magnitude of the slope signal exceeds the threshold, means for detecting when a positive slope that has been identified as exceeding the threshold is within a particular a time of a negative slope that has been identified as exceeding the threshold, where the particular time is based on expected widths of pace pulses to be detected.

9. The patient monitoring system of claim 8 further comprising means for creating a modified ECG signal in which a portion of the signal having a detected pace pulse is substantially modified.

10. The patient monitoring system of claim 9 wherein the means for creating a modified ECG signal:

(1) stores an initial threshold;

(2) replaces ECG data for a predetermined replacement period;

(3) in the replacement period, searches for a slope that exceeds the threshold, and if such slope is detected, extends the replacement period and replaces the initial threshold with a new value.

11. The patient monitoring system of claim 9 wherein the means for creating a modified ECG signal:

(1) creates a modified ECG signal from which pace pulses have been substantially removed;

(2) filters the modified ECG signal;

(3) reinserts pace pulse data in the modified ECG signal.

12. The patient monitoring system of claim 9 wherein the means for creating a modified ECG signal replaces pace pulses with fixed pace pulses.

13. The patient monitoring system of claim 8 further comprising housing enclosing said pace-pulse detector and said ECG front-end and wherein the housing is adapted to be patient-borne.

14. The patient monitoring system of claim 13 wherein the further includes a wireless communication transmitter for transmitting the ECG data.

* * * * *